US008968722B2

(12) United States Patent
Wittke

(10) Patent No.: US 8,968,722 B2
(45) Date of Patent: Mar. 3, 2015

(54) MILK-BASED NUTRITIONAL COMPOSITIONS CONTAINING LACTOFERRIN AND USES THEREOF

(71) Applicant: Mead Johnson Nutrition Company, Glenview, IL (US)

(72) Inventor: Anja Wittke, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

(21) Appl. No.: 13/718,695

(22) Filed: Dec. 18, 2012

(65) Prior Publication Data
US 2013/0150306 A1 Jun. 13, 2013

Related U.S. Application Data

(63) Continuation-in-part of application No. 12/980,813, filed on Dec. 29, 2010, now Pat. No. 8,648,036.

(51) Int. Cl.
A61K 35/74 (2006.01)
A23K 1/18 (2006.01)
A61K 31/715 (2006.01)
A61K 38/14 (2006.01)

(52) U.S. Cl.
USPC .............. 424/93.45; 426/2; 514/54; 514/20.9

(58) Field of Classification Search
USPC .................... 424/93.45; 426/2; 514/54, 20.9
See application file for complete search history.

(56) References Cited

U.S. PATENT DOCUMENTS

| | | | |
|---|---|---|---|
| 4,791,193 A | | 12/1988 | Okonogi et al. |
| 4,977,137 A | * | 12/1990 | Nichols et al. ................ 514/5.5 |
| 5,374,567 A | | 12/1994 | Cartagena |
| 5,397,591 A | | 3/1995 | Kyle et al. |
| 5,550,156 A | | 8/1996 | Kyle |
| 5,849,885 A | | 12/1998 | Nyuens et al. |
| 5,861,491 A | | 1/1999 | Nuijens et al. |
| 5,919,913 A | | 7/1999 | Nyuens et al. |
| 6,863,918 B2 | * | 3/2005 | Bindels et al. ................ 426/590 |
| 7,368,141 B2 | | 5/2008 | Lihme |
| 7,572,474 B2 | | 8/2009 | Petschow et al. |
| 2004/0121042 A1 | | 6/2004 | Kudo et al. |
| 2006/0286258 A1 | * | 12/2006 | Petschow et al. ............. 426/590 |
| 2008/0003329 A1 | | 1/2008 | Rueda et al. |
| 2012/0184484 A1 | * | 7/2012 | Wang et al. .................... 514/2.5 |

FOREIGN PATENT DOCUMENTS

| | | |
|---|---|---|
| EP | 0295009 | 12/1988 |
| EP | 2251030 | 11/2010 |
| WO | 2004026316 | 4/2004 |
| WO | 2005039319 | 5/2005 |
| WO | 2006121507 | 11/2006 |
| WO | 2006130205 | 12/2006 |
| WO | 2008047391 | 4/2008 |
| WO | 2009068549 | 5/2009 |
| WO | 2009118771 | 10/2009 |
| WO | 2011051482 | 5/2011 |
| WO | 2012091946 | 7/2012 |

OTHER PUBLICATIONS

Takeuchi et al.,"Opioid mediated suppressive effect of milk-derived lactoferrin on anxiety induced by maternal separation in neonatal rats," Society for Neuroscience Abstract Viewer and Itinerary Planner, abstract No. 385.11, 32nd annual meeting of the Society for Neuroscience, 2002.*
Appelmelk, B., et al., "Lactoferrin is a lipid A-binding protein," Infec Immun. vol. 62, No. 6, pp. 2628-2632, Jun. 1994.
Arnold, R., et al., "Bactericidal activity of human lactoferrin: Sensitivity of a variety of microorganisms," Infec Immun. vol. 28, No. 3, pp. 893-898, Jun. 1980.
Baker, E., et al., "A structural framework for understanding the multifunctional character of lactoferrin," Biochimie. 2009;91:3-10.
Bavington, C., et al., "Stopping bacterial adhesion: a novel approach to treating infections," Respiration. 2005;72:335-344.
Beddek, A., "The Lactoferrin receptor complex in gram negative bacteria," Biometals, (2010) 23:377-386.
Boehm, G. et al., "Prebiotic in Infant Formulas," J. Clin Gastroenteroal, Jul. 2004, vol. 38, Supp. 2 pp. S76-S79.
Caccavo, D., et al., "Antimicrobial and immunoregulatory functions of lactoferrin and its potential therapeutic application," J Endotox Res. 2002;8:403-417.
Das, N., et al., "Chemotherapy of mice experimentally infected with *Shigella* Ilexneri," Appl Microbiol. 1970;19:776-780.
Database GNPD [online] www.gnpd.com, Anonymous: "Stage 1 baby formula powder," Database accession No. 1395602, Sep. 2010.
Database GNPD [online] www.gnpd.com, Anonymous: "Infant formula milk powder (state 1)," Database accession No. 1337332, Jun. 2010.
Database GNPD [online] www.gnpd.com, Anonymous: "New birth formula," Database accession No. 1249000, Jan. 2010.
De Araujo, A., et al., "Lactoferrin and free secretory component of human milk inhibit the adhesion of enteropathogenic Escherichis *coli* to HeLa cells," BMC Microbiology, 2001, 1:25. http://www.biomedcentral.coml1471-21S011125.
De Oliveira, I., "Binding of lactoferrin and free secretory component to enterotoxigenic Escherichis *coli*," FEMS Microbiol Lett. 2001;203:29-33.
Di Biase, A., et al., "Effect of bovine lactoferricin on Enteropathogenic *Yersinia* adhesion and invasion in HEp-2 cells," J Med Microbiol. 2004;53:407-412.
Di Biase, A., et al., "Heparin-interacting sites of bovine lactoferrin are involved in anti-adenovirus activity," J Med Virol. 2003;69:495-502.

*Primary Examiner* — Rosanne Kosson
(74) *Attorney, Agent, or Firm* — Patterson Intellectual Property Law, P.C.; James R. Cartiglia

(57) ABSTRACT

The present disclosure relates to milk-based nutritional compositions comprising lactoferrin and/or a prebiotic component, wherein, when combined, the lactoferrin and prebiotic component may exhibit additive or synergistic beneficial effects on the health and development of a pediatric subject. The disclosure further relates to methods comprising the administration of said milk-based nutritional compositions to pediatric subjects.

10 Claims, No Drawings

(56) References Cited

OTHER PUBLICATIONS

Dionysius, D., et al., "Forms of lactoferr-in: Their antibacterial effect on enterotoxigenic *Escherichia coli*," J Dairy Sci. 1993;76:2597-2606.

Dixon, D- L., et al., "Lower interleukin-S levels in airway aspirates from breastfed infants with acute bronchiolitis," Pediatr Allergy Immunol. 2010. DOI: 10.1111j.399-3038.2010.01011.x.

Edde, L., et al., "Lactoferrin protects neonatal rats from gut-related systemic infection," Am J Physiol Gastrointest Liver Physiol. 2001;281:G 1140-G 1150.

Egashira, M., et al., "Does daily intake of bovine lactoforrin-containing products ameliorate rotaviral gastroenteritis?" Acta Paediatr. 20017;96:1242-1244.

Ellison, R., et al., "Damage of the outer membrane of enteric gram-negative bacteria by lactoferrin and transferring," Infect Immun. 1985;56:2774-2781.

Fischer, R., et al., "Regulation of physiological and pathological Th1 and Th2 responses by lactoferrin," Biochem Cell Biol, 2006;84:303-311.

Flores-Villasenor, H., et al., "Bactericidal effect of bovine lactoferrin, LFcin, LFampin and LFchimera on antibiotic-resistant *Staphylococcus aureus* and *Escherichia coli*," BioMetals. 2010;23:569-579.

Gomez, H., et al., "Lactoferrin protects rabbits from *Shigella flexneri*-Induced inflammatory enteritis," Infec Immun. 2002;70:7050-7053.

Gomez, H., et al., "Human lactoferrin impairs virulence of *Shigella flexneri*," J Infect Dis. 2003;187:87-95.

Gonzalez-Chavez, S., et al., "Lactoferrin: structure, function and applications," Intl. J Antimicrob Agents. 2009; 33;301.e1-301.e8.

Grover, M., et al., "Effect of human milk prostaglandins and lactoferrin on respiratory syncytial virus and rotavirus," Acta Paediatr. 1997;86:315-316.

Humphries et al., "Interactions of enteropathogenic *Escherichia coli* with pediatric and adult intestinal biopsy specimens during early adherence," Infect. Immun., 77, 4463-4468 (2009).

Iizumi, Y., "The Enteropathogenic *E. coli* effector EspB facilitates microvillus effacing and Antiphagocytosis by Inhibiting Myosin Function" in Cell Hosts and Microbe, pp. 383-392 (2007).

Kawasaki, Y., et al., "Inhibitory effects of bovine lactoferrin on the adherence of Enterotoxigenic *Escherichia coli* to host cells," Biosci Biotechnol Biochem. 2000;64:348-354.

King, Jr. J., et al., "A double-blind, placebo-controlled, pilot study of bovine lactoferrin supplementation in bottle-fed infants," J Pediatr Gastroenterol Nutr. 2007;44:245-251.

Kullen, M.J. et al., "The Delivery of Probiotics and Prebiotics to Infants," Current Pharmaceutical Design, 2005, vol. 11, pp. 55-74.

Kvistgaard, A., et al., "Inhibitory effects of human and bovine milk constituents on rotavirus infections,". J Dairy Sci. 2004;87:4088-4096.

Legrand, D. et al., "Interactions of lactoferrin with cells involved in immune function," Biochem Cell Biol. 2006;84:282-290.

Legrand, D. et al., "Lactoferrin: a modulator of immune and inflammatory responses," Cell Mol Life Sci. 2005;62:2549-2559.

Ling, J. et al., "Perspectives on Interactions Between Lactoferrin and Bacteria," Biochemistry and Cell Biology, pp. 275-281 (2006).

Lonnerdal, B., "Nutritional and physiologic significance of human milk proteins," Am J Clin Nutr. 2003;77: 15378-15438.

Mange, J.P., et al., "Adhesive properties of *Enterobacter sakazakii* to human epithelial and brain microvascular endothelial cells," BMC Microbiol. 2006;6:58-68.

McCann, K., et al., "The effect of bovine lactoferrin and lactoferricin B on the ability of feline Calcivirus (a norovirus surrogate) and poliovirus to infect cell cultures," J Appl Microbiol. 2003;95:1026-1033.

Meijias, A., et al., "Respiratory syncytial virus persistence evidence in the mouse model," Pediatr Infect Dis J. 2008;27:S60-S62.

Miyauchi, H., et al., "Bovine lactoferrin stimulates the phagocytic activity of human neutrophils: Identification of its active domain," Cell Immunol. 1998;187:34-37.

Mosquito, S., et al., "Effect of bovine lactoferrin in *Salmonella* ser. *typhimurium* infection in mice," BioMetals. DOI I0.1007/s10534-010-9325-1, Mar. 21, 2010.

Mulder, A., et al., "Bovine lactoferrin supplementation supports immune and antioxidant status in healthy human males," Nutr Res. 2008;28:583-589.

Naidu, S., et al., Relationship between antibacterial activity and porin binding of lactoferrin in *Escherichia coli* and *Salmonella typhimurium*, Antimicrob Agents and Chemother 1993;37:240-245.

Notice of Opposition to European Patent Application No. 1887888.

Ochoa, T., "Lactoferrin Impairs Type III Secretory System Function in Enteropathogenic *Escherichia coli*," Infection and Immunity, pp. 5149-5155 (2003).

Ochoa, T., et al., "Effect of lactoferrin on enteric pathogens," Biochime. 2009;91:30-34.

Ochoa, T., et al., "Effect of lactoferrin on Enteroaggregative *E. coli* (EAEC)," Biochem Cell Biol. 2006;84:369-376.

Ochoa, T., et al., "Lactoferrin disruption of bacterial type III secretion systems," BioMetals. 2004;17:257-260.

Ochoa, T., et al., "Impact of lactoferrin supplementation on growth and prevalence of *Giardia* colonization in children," Clin Infect Dis. 2008;46:1881-1883.

Orsi, N., "The antimicrobial activity of lactoferrin: Current status and perspectives," BioMetals 17: 189-196, 2004.

Perez-Cano, F., et al., "Supplementing suckling rats with whey protein concentrate modulates the immune response and ameliorates rat rotavirus-induced diarrhea," J Nutr. 2008;138:2392-2398.

Pietrantoni, A., et al., "Bovine lactoferrin inhibits adenovirus infection by interacting with viral structural polypeptides," Antimicrob Agent Chemother. 2003;47:2688-2691.

Portelli, J., et al., "Effects of compounds with antibacterial activities in human milk on respiratory syncytial virus and cytomegalovirus in vitro," J Med Microbiol. 1998;47:1015-1018.

Qiu, J. et al., Human milk lactoferrin inactivates two putative colonization factors expressed by *Haemophilus influenza*, Proc Natl Acad Sci USA. 1998;95:12641-12646.

Quintero, M., et al., "Adherence inhibition of *Cronobacter sakazakii* to intestinal epithelial cells by pre biotic oligosaccharides,". Cur Microbiol. 2011; DOI: 10.1007/s00284-011-9882-8. Jan. 17, 2011.

Reagan-Shaw, S., et al., "Dose translation from animal to human studies revisited," FASEB J. 2008:22:659-661.

Roine, I., et al., "Breastfeeding reduces immune activation in primary respiratory syncytial virus infection," Eur Cytokine Network. 2005;16:206-210.

Sano, H., et al., "Lactoferrin and surfactant protein A exhibit distinct binding specificity to F protein and differently modulate respiratory syncytial virus infection," Eur J Immunol. 2003;33:2894-2902.

Santapaola, D., et al., "Effect on bovine lactoferrin on the activation of the enteroinvasive bacterial type III secretion system," BioMetals. 17: 261-265, 2004.

Sfier, R., et al., "The mode of oral bovine lactoferrin administration influences mucosal and systemic immune responses in mice," J Nutr. 2004;134:403-409.

Sharon, N., et al., "Safe as mother's milk: carbohydrates as future anti-adhesion drugs for bacterial diseases," Glycoconjugate J. 2000; 17, 659-664.

Shin, K. et al., "Effects of orally administered bovine lactoferrin and lactoperoxidase on influenza virus infection in mice," J Med Micor (2005), 54, 717-723.

Shin, K., et al., Antibacterial activity of bovine lactoferrin and its peptides against enterohaemorrhagic *Escherihia coli* O157:H7, Lett Appl Microbiol. 1998;26:407-411.

Shoaf K., et al., "Prebiotic galactooligosaccharides to reduce adherence of Enteropathogenic *Escherichia coli* to tissue culture cells," Infect Immun. 2006;74:6920-6928.

Shoaf-Sweeney, K., et al., "Adherence, anti-adherence, and oligosaccharides: preventing pathogens from sticking to the host," Adv Food Nutr Res. 2009;55:101-161.

Spadaro, M., et al., "Lactoferrin, a major defense protein of innate immunity, is a novel maturation factor for human dendritic cells," FASEB J. 2008;22:2747-2757.

(56) References Cited

OTHER PUBLICATIONS

Superti, F., et al., "Involvement of bovine lactoferrin metal saturation, sialic acid and protein fragments in the inhibition of rotavirus infection," Biochim Biophys Acta. 2001;1528:107-115.

Suzuki, Y., et al., "Molecular cloning and functional expression of a human intestinal lactoferrin receptor," Biochemistry. 2001;40:15771-15779.

Suzuki, Y., et al., "The N1 domain of human lactoferrin is required for internalization by Caco-2 cells and targeting to the nucleus," Biochemistry. 2008;47:10915-10920.

Suzuki, Y., et al., "Mammalian lactoferrin receptors: structure and function," Cell Mol Life Sci. 2005;62:2560-2575.

Suzuki, Y., et al., "Baculovirus expression of mouse lactoferrin receptor and tissue distribution in the mouse," BioMetals 17:301-309, 2004.

Takakura, N., et al., "Influences of orally administered lactoferrin on IFN-y and IL-10 production by intestinal intraepithelial lymphocytes and mesenteric lymph-node cells," Biochem Cell Biol. 2006;84:363-368.

Van Der Strate, B., et al., "Antiviral activities of lactoferrin," Antiviral Research. 2001;225-239.

Wakabayashi, H., et al., "Modulation of immunity-related gene expression in small intestines of mice by oral administration of lactoferrin,". Clin Vaccine Immunol. 2006;13:239-245.

Weaver, L. "Improving Infant Milk Formulas: Near the End of the Trail for the Holy Grail?" Journal of Pediatric Gastroenterology and Nutrition, Mar. 2003, vol. 36, pp. 301-310.

Yamauchi, K., et al., "Effects of orally administered bovine lactoferrin on the immune system of healthy volunteers," In: Advances in Lactoferrin Research. 1998, vol. 443, pp. 261-265.

Yamauchi, K., et al., "Bovine lactoferrin: benefits and mechanisms of action against infections," Biochem Cell Biol. 2006;84:291-296.

Yamauchi, K., et al., "Antibacterial activity of lactoferrin and a pepsin-derived lactoferrin peptide fragment," Infec Immun. 2993;61:719-728.

Zhang, G., "Neutralization of Endotoxin In Vitro and In Vivo by a Human Lactoferrin-Derived Peptide," Infection and Immunity, vol. 67, No. 3, p. 1353-1358, Mar. 1999.

Bemiller, J., "An Introduction to Pectins: Structure and Properties," Chemistry and Function of Pectins; Chapter 1; 1986.

Fanaro, S. et al., "Acidic Oligosaccharides from Pectin Hydrolysate as New Component for Infant Formulae: Effect on Intestinal Flora, Stool Characteristics, and pH," Journal of Pediatric Gastroenterology and Nutrition, 41: 186-190, Aug. 2005.

Kunz, C. et al., "Oligosaccharides in Human Milk: Structure, Functional, and Metabolic Aspects," Ann Rev. Nutr. 20:699-722 (2000).

Anonymous, Infant formula milk powder, Mintel, Jun. 2010.

Takeuchi, T., et al., "Opioid mediated suppressive effect of milk-derived lactoferrin on distress induced by maternal separation in rat pups," Brain Research, vol. 979, Issues 1-2, Jul. 25, 2003, pp. 216-224.

* cited by examiner

MILK-BASED NUTRITIONAL COMPOSITIONS CONTAINING LACTOFERRIN AND USES THEREOF

CROSS-REFERENCE TO RELATED APPLICATIONS

This application is a continuation in part of U.S. patent application Ser. No. 12/980,813, filed Dec. 29, 2010, the disclosure of which is incorporated herein by reference.

TECHNICAL FIELD

The present disclosure relates generally to milk-based nutritional compositions comprising lactoferrin that are suitable for administration to pediatric subjects. Additionally, the disclosure relates to methods of supporting and promoting gastrointestinal health, immune function, cognitive development and brain function and to a method of reducing psychological stress in a pediatric subject via administration of a milk-based nutritional composition comprising lactoferrin and a prebiotic component, wherein the lactoferrin and the prebiotic component may exhibit additive and/or synergistic beneficial effects.

BACKGROUND ART

Lactoferrin, an iron-binding glycoprotein, is one of the major multifunctional agents present in human milk. It has the capacity to bind two molecules of iron in a reversible fashion and can facilitate the uptake of iron within the intestines. Further, lactoferrin has been shown to be both bacteriostatic and bactericidal, and it aids in preventing intestinal infections in humans, especially in pediatric subjects.

Moreover, human lactoferrin has been reported to protect against Gram-negative bacteria in a variety of ways. It is believed that human lactoferrin exerts a bacteriostatic activity by depriving microorganisms of the iron that is necessary for growth. Thus, by sequestering the environmental iron of pathogenic microorganisms, human lactoferrin effectively inhibits the growth of those microorganisms.

Several studies have examined the effect of human lactoferrin on various bacterial species. For example, a 2001 study demonstrated that human lactoferrin can inhibit the adhesion of EPEC to HeLa cells. Nascimento de Arujao, A., et al., *Lactoferrin and Free Secretory Component of Human Milk Inhibit the Adhesion of Enteropathogenic Escherichia coli to HeLa Cells*, BMC Microbiol. 1:25 (2001).

Further, human lactoferrin appears to have a positive effect on the symptoms of diarrheal diseases. Yet some women are unwilling or unable to breastfeed. Accordingly, in an effort to mimic breast milk, it would be beneficial to provide a nutritional composition for a pediatric subject that contains lactoferrin from a non-human source. However, the addition of lactoferrin to commercially viable nutritional compositions has generally been limited due to lactoferrin's proclivity to lose functional capacity during formula processing steps that involve significant fluctuation in temperature and/or pH.

Moreover, the infant gut microflora is rapidly established in the first few weeks following birth, and it has a great impact on an infant's immune system. The nature of this intestinal colonization is initially determined by early exposure to environmental sources of microbes and by the general state of health of the infant. Whether the infant is breast-fed or formula-fed also has a strong influence on the intestinal bacterial population.

Human milk contains a number of factors that may contribute to the growth and population of the gut microflora of infants. Among these factors is a complex mixture of more than 130 different oligosaccharides that reach levels as high as 8-12 g/L in transitional and mature milk. Kunz, et al., *Oligosaccharides in Human Milk Structure, Functional, and Metabolic Aspects*, Ann. Rev. Nutr. 20: 699-722 (2000). These oligosaccharides are resistant to enzymatic digestion in the upper gastrointestinal tract and reach the colon intact, where they then serve as substrates for colonic fermentation.

Cow's milk and commercially available infant formulas that are based on cow's milk provide only trace amounts of oligosaccharides; as a result, prebiotics may be used to supplement the diet of formula-fed infants. Prebiotics have been defined as non-digestible food ingredients that beneficially affect the host by selectively stimulating the growth and/or activity of one or a limited number of cells in the colon that can improve the health of the host.

Both the interaction among dietary components and among the microflora of the intestinal ecosystem are very complex. Consequently, then, the matrix of an infant formula or other pediatric nutritional composition may influence the effectiveness of prebiotics when such ingredients are provided as supplements in the diet of a formula-fed infant. Further, the type and concentration of proteins used in a formula matrix may also modulate the intestinal microbiota. Because human milk is the preferred source of infant nutrition, it is desirable to provide a formula matrix that mimics the qualities of human milk by allowing for effective supplementation of prebiotics as functional food ingredients.

Accordingly, it would be beneficial to provide a nutritional composition for pediatric subjects that contains both lactoferrin and prebiotics.

BRIEF SUMMARY

Briefly, the present disclosure is directed, in an embodiment, to a method for modulating psychological stress in a pediatric subject, the method comprising administering to the pediatric subject a milk-based nutritional composition comprising lactoferrin from a non-human source. In certain embodiments, the method comprises administering:

a. up to about 7 g/100 kcal of a fat or lipid source, more preferably about 3 g/100 kcal to about 7 g/100 kcal of a fat or lipid source;

b. up to about 5 g/100 kcal of a protein source, more preferably about 1 g/100 kcal to about 5 g/100 kcal of a protein source;

c. at least about 10 mg/100 kcal of lactoferrin, more preferably from about 70 mg/100 kcal to about 220 mg/100 kcal of lactoferrin, and most preferably about 90 mg/100 kcal to about 190 mg/100 kcal of lactoferrin; and d. about 0.1 g/100 kcal to about 1 g/100 kcal of a prebiotic composition comprising polydextrose and/or galactooligosaccharide.

In certain embodiments, the disclosure is directed to a method for modulating plasma corticosterone levels in a pediatric subject, the method comprising administering to the pediatric subject a milk-based nutritional composition comprising bovine lactoferrin.

In some embodiments, the disclosure is directed to a method for supporting gastrointestinal development in a pediatric subject, the method comprising administering to the pediatric subject a milk-based nutritional composition comprising bovine lactoferrin and a prebiotic component comprising polydextrose.

In still other embodiments, the disclosure is directed to methods for supporting healthy growth and development in a pediatric subject by administering to the subject a nutritional composition comprising lactoferrin and at least one prebiotic.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to milk-based nutritional compositions comprising lactoferrin that are suitable for administration to a pediatric subject. Additionally, the disclosure relates to methods of supporting and promoting gastrointestinal health, immune function, cognitive development and brain function and to methods of reducing psychological stress in a pediatric subject via administration of milk-based nutritional compositions comprising lactoferrin and a prebiotic component.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the 37th week of gestation. "Late preterm" means an infant form between the 34th week and the 36th week of gestation. "Full term" means an infant born after the end of the 37th week of gestation. "Low birth weight infant" means an infant born weighing less than 2500 grams (approximately 5 lbs, 8 ounces). "Very low birth weight infant" means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

The term "degree of hydrolysis" refers to the extent to which peptide bonds are broken by a hydrolysis method.

The term "partially hydrolyzed" means having a degree of hydrolysis which is greater than 0% but less than about 50%.

The term "extensively hydrolyzed" means having a degree of hydrolysis which is greater than or equal to about 50%.

The term "protein-free" means containing no measurable amount of protein, as measured by standard protein detection methods such as sodium dodecyl(lauryl)sulfate-polyacrylamide gel electrophoresis (SDS-PAGE) or size exclusion chromatography. In some embodiments, the nutritional composition is substantially free of protein, wherein "substantially free" is defined hereinbelow.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts a beneficial effect on the health of the host.

The term "inactivated probiotic" means a probiotic wherein the metabolic activity or reproductive ability of the referenced probiotic has been reduced or destroyed. The "inactivated probiotic" does, however, still retain, at the cellular level, at least a portion its biological glycol-protein and DNA/RNA structure. As used herein, the term "inactivated" is synonymous with "non-viable".

"Prebiotic" means a non-digestible food ingredient that beneficially affects the host by selectively stimulating the growth and/or activity of one or a limited number of bacteria in the digestive tract that can improve the health of the host.

"Phytonutrient" means a chemical compound that occurs naturally in plants. Phytonutrients may be included in any plant-derived substance or extract. The term "phytonutrient(s)" encompasses several broad categories of compounds produced by plants, such as, for example, polyphenolic compounds, anthocyanins, proanthocyanidins, and flavan-3-ols (i.e. catechins, epicatechins), and may be derived from, for example, fruit, seed or tea extracts. Further, the term phytonutrient includes all carotenoids, phytosterols, thiols, and other plant-derived compounds. Moreover, as a skilled artisan will understand, plant extracts may include phytonutrients, such as polyphenols, in addition to protein, fiber or other plant-derived components. Thus, for example, apple or grape seed extract(s) may include beneficial phytonutrient components, such as polyphenols, in addition to other plant-derived substances.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

"Pectin" means any naturally-occurring oligosaccharide or polysaccharide that comprises galacturonic acid that may be found in the cell wall of a plant. Different varieties and grades of pectin having varied physical and chemical properties are known in the art. Indeed, the structure of pectin can vary significantly between plants, between tissues, and even within a single cell wall. Generally, pectin is made up of negatively charged acidic sugars (galacturonic acid), and some of the acidic groups are in the form of a methyl ester group. The degree of esterification of pectin is a measure of the percentage of the carboxyl groups attached to the galactopyranosyluronic acid units that are esterified with methanol.

Pectin having a degree of esterification of less than 50% (i.e., less than 50% of the carboxyl groups are methylated to form methyl ester groups) are classified as low-ester, low methoxyl, or low methylated ("LM") pectins, while those having a degree of esterification of 50% or greater (i.e., more than 50% of the carboxyl groups are methylated) are classified as high-ester, high methoxyl or high methylated ("HM") pectins. Very low ("VL") pectins, a subset of low methylated pectins, have a degree of esterification that is less than approximately 15%.

"Pathogen" means an organism that causes a disease state or pathological syndrome. Examples of pathogens may include bacteria, viruses, parasites, fungi, microbes or combination(s) thereof.

"Modulate" or "modulating" means exerting a modifying, controlling and/or regulating influence. In some embodiments, the term "modulating" means exhibiting an increasing or stimulatory effect on the level/amount of a particular component. In other embodiments, "modulating" means exhibiting a decreasing or inhibitory effect on the level/amount of a particular component.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to milk-based nutritional compositions comprising lactoferrin and/or a prebiotic component, to uses thereof, and to methods comprising administration of those nutritional compositions. The nutritional compositions of the present disclosure support overall health and development in a pediatric human subject, such as an infant (preterm and/or term) or a child.

The intestinal microflora plays a crucial role in the postnatal development of most gastrointestinal functions and also in the development of the gut-associated immune system in pediatric subjects. Accordingly, the nutritional composition of the present disclosure supports gastrointestinal health and development. Moreover, a healthy intestinal flora supports an adequate gut-brain communication, affecting brain function and, consequently, psychological stress responses, resulting in modified behavior. Administration of a prebiotic component and lactoferrin together can modulate the intestinal flora of a pediatric subject by increasing beneficial bacteria and/or reducing adhesion of pathogens in the gastrointestinal system. Thus, in some embodiments, the present disclosure is directed to a method for modulating psychological stress responses via administration of at least one prebiotic component and lactoferrin. And in certain embodiments, the combination of prebiotic(s) and lactoferrin has additive and/or synergistic beneficial effects that support gastrointestinal development. In certain embodiments, the disclosure is related to a method for supporting gastrointestinal health and/or development in a pediatric subject. The method comprises administering lactoferrin and at least one prebiotic to a pediatric subject.

In some embodiments, the present disclosure is directed to a method of increasing fecal secretory IgA in a pediatric subject by administering to the subject a nutritional composition comprising a prebiotic component and lactoferrin. In certain embodiments, the present disclosure is directed to a method for modulating gastric emptying and/or improving intestinal tolerance of enteral feeding in a pediatric subject, the method(s) comprising administering a nutritional composition comprising a combination of a prebiotic component and lactoferrin. In still other embodiments, the present disclosure is directed to a method for reducing stool viscosity in a pediatric subject by administering an effective amount of a prebiotic component together with lactoferrin.

Additionally, the present disclosure is directed to a method for reducing the occurrence of necrotizing enterocolitis (NEC) in a pediatric subject, the method comprising administering a prebiotic component and lactoferrin to a pediatric subject. In some embodiments, the reduced occurrence of NEC is associated with improvement in formation of an intestinal mucus layer in an infant via administration of lactoferrin. More specifically, the inventors of the present application have discovered that ileal production of mucin(s) may be increased in an infant when a nutritional composition comprising lactoferrin is administered to said infant. Thus, in some embodiments, the present disclosure is directed to a method for improving mucus layer formation in an infant, the method comprising administering an effective amount of lactoferrin to the infant. In other embodiments, the present disclosure is directed to a method for increasing ileal production of mucin in a pediatric subject by administering a nutritional composition comprising lactoferrin and at least one prebiotic to the pediatric subject.

Moreover, during early life, infants and children experience many stressful situations due to, for example, a changing environment or being hungry or tired. Consequently, stress hormones are released, which may negatively affect brain development and/or cause other long-term detrimental effects in a pediatric subject. Yet the inventors of the present disclosure have discovered that administration of lactoferrin to a pediatric subject can reduce or suppress psychological stress and/or modulate plasma corticosterone levels, thereby promoting healthy brain and cognitive growth and development in a pediatric subject.

Thus, in some embodiments, the present disclosure includes a method for reducing psychological stress in a pediatric subject comprising administering to the subject an effective amount of lactoferrin. In other embodiments, the disclosure includes a method for modulating plasma corticosterone levels in a pediatric subject, comprising administering to the pediatric subject an effective amount of lactoferrin. In still other embodiments, the disclosure is directed to a method for improving brain and/or cognitive function in a pediatric subject by administering an effective amount of lactoferrin to the subject. In certain embodiments, the lactoferrin is administered together with a prebiotic component that has additive and/or synergistic beneficial effects when combined with the lactoferrin.

In some embodiments, brain development, brain functionality and, therefore, behavior may be modulated in a subject via administration of lactoferrin. Additionally, administration of lactoferrin may affect the hypothalamic-pituitary adrenal axis (HPA), its communication with the gastrointestinal system, the brain and/or other body systems. In infants, immaturity of the gut often causes gastrointestinal symptoms that affect their nutritional status with consequences for their overall health. The present disclosure is directed to a nutritional composition that provides, in some embodiments, bovine lactoferrin and at least one probiotic, wherein administration of said nutritional composition modifies gut development and communication of the gut with the brain via the gut-brain axis. Moreover, the nutritional compositions of the present disclosure may positively impact brain-related functions. Thus, in some embodiments, the present disclosure is directed to a method of modulating gut-brain communication, the method comprising administering to a pediatric subject a nutritional composition comprising lactoferrin.

In certain other embodiments, the nutritional composition comprises a combination of *Lactobacillus helveticus* and *Bifidobacterium longum*. Administration of a nutritional composition comprising these probiotics to a pediatric subject may result in reduced anxiety in the subject and/or in decreased serum cortisol in the subject, thereby indicating beneficial psychological effects. Accordingly, the present disclosure is directed, in some embodiments, to a method for reducing anxiety in a subject, wherein the method comprises at least the step of administering a nutritional composition comprising at least one probiotic selected from the group consisting of *Lactobacillus helveticus* and *Bifidobacterium longum* to a subject. In some embodiments, the present disclosure is directed to a method for decreasing serum cortisol in a subject, the method comprising administering a nutritional composition comprising lactoferrin and at least one probiotic selected from the group consisting of *Lactobacillus helveticus* and *Bifidobacterium longum* to the subject.

Further, in some embodiments, the nutritional composition may comprise *Lactobacillus rhamnosus*. Administration of *Lactobacillus rhamnosus* to a pediatric subject may reduce stress-induced corticosterone levels, thereby reducing the occurrence of anxiety and/or of depression-related behaviors. As such, in some embodiments, the present disclosure is directed to a method of reducing stress-induced corticosterone levels in a subject via administration of a nutritional composition comprising *Lactobacillus rhamnosus* to the subject.

In other embodiments, administration of lactoferrin modulates the intestinal barrier function in a subject. Moreover, in some embodiments, administration of lactoferrin modulates the immune system. In further embodiments, administration of lactoferrin modulates the opioid system. And in particular embodiments, lactoferrin behaves as an opioid antagonist. In still other embodiments, lactoferrin modulates other physiological processes, including satiety, food intake, and regulation of glucose and/or fat metabolism.

Furthermore, infants, particularly preterm infants, are often faced with severe infections, such as sepsis, pneumonia and urinary tract infection(s). Accordingly, as a result of the beneficial additive and/or synergistic effects of administration of a prebiotic component together with lactoferrin, preterm morbidity may be reduced. Therefore, in some embodiments, the present disclosure is directed to a method of reducing morbidity in a preterm infant, comprising administering a nutritional composition comprising lactoferrin to a preterm infant.

As used herein, "lactoferrin from a non-human source" means lactoferrin which is produced by or obtained from a source other than human breast milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism. The term "non-human lactoferrin", as used herein, refers to lactoferrin having an amino acid sequence that is different than the amino acid sequence of human lactoferrin.

Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) and 28 to 31 (RKVR) are arginine-rich cationic domains in the N-terminus especially critical to the antimicrobial activities of lactoferrin. A similar region in the N-terminus is found in bovine lactoferrin (residues 17 to 42; FKCRRWQWRMKKLGAPSITCVRRAFA).

As described in "*Perspectives on Interactions Between Lactoferrin and Bacteria*" which appeared in the publication BIOCHEMISTRY AND CELL BIOLOGY, pp 275-281 (2006), lactoferrins from different host species may vary in their amino acid sequences though commonly possess a relatively high isoelectric point with positively charged amino acids at the end terminal region of the internal lobe. Suitable lactoferrins for use in the present disclosure include those having at least 48% homology with the amino acid sequence AVGEQELRKCN-QWSGL at the HLf (349-364) fragment. In some embodiments, the lactoferrin has at least 65% homology with the amino acid sequence AVGEQELRKCNQWSGL at the HLf (349-364) fragment, and, in embodiments, at least 75% homology. For example, non-human lactoferrins acceptable for use in the present disclosure include, without limitation, bovine lactoferrin, porcine lactoferrin, equine lactoferrin, buffalo lactoferrin, goat lactoferrin, murine lactoferrin and camel lactoferrin.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In one embodiment, lactoferrin is present in the nutritional composition in an amount of at least about 10 mg/100 kCal. In certain embodiments, the nutritional composition may include between about 10 and about 240 mg lactoferrin per 100 kCal. In another embodiment, where the nutritional composition is an infant formula, the nutritional composition may comprise lactoferrin in an amount of from about 70 mg to about 220 mg lactoferrin per 100 kCal; in yet another embodiment, the nutritional composition may comprise about 90 mg to about 190 mg lactoferrin per 100 kCal. In still other embodiments, the nutritional composition may comprise about 5 mg to about 16 mg lactoferrin per 100 kcal. In further embodiments, the nutritional composition comprises about 9 mg to about 14 mg lactoferrin per 100 kcal.

In some embodiments, the nutritional composition can include lactoferrin in the quantities of from about 0.5 mg to about 1.5 mg per milliliter of formula. In nutritional compositions replacing human milk, lactoferrin may be present in quantities of from about 0.6 mg to about 1.3 mg per milliliter of formula. In certain embodiments, the nutritional composition may comprise between about 0.1 and about 2 grams lactoferrin per liter. In some embodiments, the nutritional composition includes between about 0.5 and about 1.5 grams lactoferrin per liter of formula.

The nutritional compositions described herein can, in some embodiments comprise non-human lactoferrin, non-human lactoferrin produced by a genetically modified organism and/or human lactoferrin produced by a genetically modified organism. Lactoferrin is generally described as an 80 kilodalton glycoprotein having a structure of two nearly identical lobes, both of which include iron binding sites. As described in "*Perspectives on Interactions Between Lactoferrin and Bacteria*" which appeared in the publication BIOCHEMISTRY AND CELL BIOLOGY, pp 275-281 (2006), lactoferrin from different host species may vary in an amino acid sequence, though it commonly possesses a relatively high isoelectric point with positively charged amino acids at the end terminal region of the internal lobe. Lactoferrin has been recognized as having bactericidal and antimicrobial activities.

Surprisingly, the forms of lactoferrin included herein maintain relevant activity even if exposed to a low pH (i.e., below about 7, and even as low as about 4.6 or lower) and/or high temperatures (i.e., above about 65° C., and as high as about 120° C., conditions which would be expected to destroy or severely limit the stability or activity of human lactoferrin or recombinant human lactoferrin. These low pH and/or high temperature conditions can be expected during certain processing regimen for nutritional compositions of the types described herein, such as pasteurization.

In some embodiments, the nutritional composition of the present disclosure comprises bovine lactoferrin. Bovine lactoferrin (bLF) is a glycoprotein that belongs to the iron transporter or transferring family. It is isolated from bovine milk, wherein it is found as a component of whey. There are known differences between the amino acid sequence, glycosylation patters and iron-binding capacity in human and bovine lactoferrin. Additionally, there are multiple and sequential processing steps involved in the isolation of bovine lactoferrin from cow's milk that affect the physiochemical properties of the resulting bovine lactoferrin preparation. Human and bovine lactoferrin are also reported to have differences in their abilities to bind the lactoferrin receptor found in the human intestine.

In certain embodiments, the bLF has been isolated from whole milk having a low somatic cell count. In some embodiments, "low somatic cell count" refers to a concentration of less than 200,000 cells/mL.

Though not wishing to be bound by this or any other theory, it is believe that bLF that has been isolated from whole milk has less lipopolysaccharide (LPS) initially bound than does bLF that has been isolated from milk powder. Additionally, it is believed that bLF with a low somatic cell count has less initially-bound LPS. A bLF with less initially-bound LPS has more binding sites available on its surface. This is thought to aid bLF in binding to the appropriate location and disrupting the infection process.

The bLF that is used in certain embodiments may be any bLF isolated from whole milk and/or having a low somatic cell count, wherein "low somatic cell count" refers to a somatic cell count less than 200,000 cells/mL. By way of example, suitable bLF is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

In an embodiment, the bLF may be administered via a solution, capsule, tablet or caplet. Carriers for bLF can have a bLF concentration of between about 0.01% and about 100%.

The nutritional composition may also contain one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising polydextrose ("PDX") In some embodiments, the prebiotic component comprises at least 20% w/w PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.1 mg/100 kcal to about 0.5 mg/100 kcal or about 0.3 mg/100 kcal.

In other embodiments, the prebiotic component may comprise galacto-oligosaccharide (GOS). If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal. In other embodiments, the amount of GOS in the nutritional composition may be from about 0.1 mg/100 kcal to about 1.0 mg/100 kcal or from about 0.1 mg/100 kcal to about 0.5 mg/100 kcal.

In a particular embodiment of the present invention, PDX is administered in combination with GOS.

In a particular embodiment, GOS and PDX are supplemented into the nutritional composition in a total amount of at least about 0.2 mg/100 kcal or about 0.2 mg/100 kcal to about 1.5 mg/100 kcal. In some embodiments, the nutritional composition may comprise GOS and PDX in a total amount of from about 0.6 to about 0.8 mg/100 kcal.

Moreover, the nutritional composition(s) of the disclosure may comprise at least one protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins are may be partially hydrolyzed or extensively hydrolyzed. In still other embodiments, the protein source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Some people exhibit allergies or sensitivities to intact proteins, i.e. whole proteins, such as those in intact cow's milk protein or intact soy protein isolate-based formulas. Many of these people with protein allergies or sensitivities are able to tolerate hydrolyzed protein. Hydrolysate formulas (also referred to as semi-elemental formulas) contain protein that has been hydrolyzed or broken down into short peptide fragments and amino acids and as a result is more easily digested. In people with protein sensitivities or allergies, immune system associated allergies or sensitivities often result in cutaneous, respiratory or gastrointestinal symptoms such as vomiting and diarrhea. People who exhibit reactions to intact protein formulas often will not react to hydrolyzed protein formulas because their immune system does not recognize the hydrolyzed protein as the intact protein that causes their symptoms.

Some gliadins and bovine caseins may share epitopes recognized by anti-gliadin IgA antibodies. Accordingly, then, the nutritional composition of the present disclosure reduces the incidence of food allergy, such as, for example, protein allergies and, consequently, the immune reaction of some patients to proteins such as bovine casein, by providing a protein component comprising hydrolyzed proteins, such as hydrolyzed whey protein and/or hydrolyzed casein protein. A hydrolyzed protein component contains fewer allergenic epitopes than an intact protein component.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 20% to about 80%, or from about 30% to about 80%, or even from about 40% to about 60%. The degree of hydrolysis is the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed. The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

As previously mentioned, persons who exhibit sensitivity to whole or intact proteins can benefit from consumption of nutritional formulas containing hydrolyzed proteins. Such sensitive persons may especially benefit from the consumption of a hypoallergenic formula.

In some embodiments, the nutritional composition of the present disclosure is substantially free of intact proteins. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

Another alternative for pediatric subjects, such as infants, that have food allergy and/or milk protein allergies is a protein-free nutritional composition based upon amino acids. Amino acids are the basic structural building units of protein. Breaking the proteins down to their basic chemical structure by completely pre-digesting the proteins makes amino acid-based formulas the most hypoallergenic formulas available.

In a particular embodiment, the nutritional composition is protein-free and contains free amino acids as a protein equivalent source. In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 kcal. In an embodiment, 100% of the free amino acids have a molecular weight of less than 500 Daltons. In this embodiment, the nutritional formulation may be hypoallergenic.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein source per 100 kcal. In other embodiments, the nutritional composition comprises between about 3.5 g and about 4.5 g of protein per 100 kcal.

Moreover, the nutritional composition of the present disclosure may comprise at least one starch or starch component. A starch is a carbohydrate composed of two distinct polymer fractions: amylose and amylopectin. Amylose is the linear fraction consisting of α-1,4 linked glucose units. Amylopectin has the same structure as amylose, but some of the glucose units are combined in an α-1,6 linkage, giving rise to a branched structure. Starches generally contain 17-24% amylose and from 76-83% amylopectin. Yet special genetic varieties of plants have been developed that produce starch with unusual amylose to amylopectin ratios. Some plants produce starch that is free of amylose. These mutants produce starch granules in the endosperm and pollen that stain red with iodine and that contain nearly 100% amylopectin. Predominant among such amylopectin producing plants are waxy corn, waxy sorghum and waxy rice starch.

The performance of starches under conditions of heat, shear and acid may be modified or improved by chemical modifications. Modifications are usually attained by introduction of substituent chemical groups. For example, viscosity at high temperatures or high shear can be increased or stabilized by cross-linking with di- or polyfunctional reagents, such as phosphorus oxychloride.

In some instances, the nutritional compositions of the present disclosure comprise at least one starch that is gelatinized or pregelatinized. As is known in the art, gelatinization occurs when polymer molecules interact over a portion of their length to form a network that entraps solvent and/or solute molecules. Moreover, gels form when pectin molecules lose some water of hydration owing to competitive hydration of cosolute molecules. Factors that influence the occurrence of gelation include pH, concentration of cosolutes, concentration and type of cations, temperature and pectin concentration. Notably, LM pectin will gel only in the presence of divalent cations, such as calcium ions. And among LM pectins, those with the lowest degree of esterification have the highest gelling temperatures and the greatest need for divalent cations for crossbridging.

Meanwhile, pregelatinization of starch is a process of pre-cooking starch to produce material that hydrates and swells in cold water. The precooked starch is then dried, for example by drum drying or spray drying. Moreover the starch of the present disclosure can be chemically modified to further extend the range of its finished properties. The nutritional compositions of the present disclosure may comprise at least one pregelatinized starch.

Native starch granules are insoluble in water, but, when heated in water, native starch granules begin to swell when sufficient heat energy is present to overcome the bonding forces of the starch molecules. With continued heating, the granule swells to many times its original volume. The friction between these swollen granules is the major factor that contributes to starch paste viscosity.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose, rice starch comprises an amylose: amylopectin ratio of about 20:80, and waxy rice starch comprises only about 2% amylose. Further, tapioca starch generally comprises about 15% to about 18% amylose, and wheat starch has an amylose content of around 25%.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Additionally, the nutritional compositions of the present disclosure comprise at least one source of pectin. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counterions.

Moreover, pectin has a unique ability to form gels. Generally, under similar conditions, a pectin's degree of gelation, the gelling temperature, and the gel strength are proportional to one another, and each is generally proportional to the molecular weight of the pectin and inversely proportional to the degree of esterification. For example, as the pH of a pectin solution is lowered, ionization of the carboxylate groups is repressed, and, as a result of losing their charge, saccharide molecules do not repel each other over their entire length. Accordingly, the polysaccharide molecules can associate over a portion of their length to form a gel. Yet pectins with increasing degrees of methylation will gel at somewhat higher pH because they have fewer carboxylate anions at any given pH. (J. N. Bemiller, *An Introduction to Pectins: Structure and Properties*, Chemistry and Function of Pectins; Chapter 1; 1986.)

The nutritional composition may comprise a gelatinized and/or pregelatinized starch together with pectin and/or gelatinized pectin. While not wishing to be bound by this or any other theory, it is believed that the use of pectin, such as LM pectin, which is a hydrocolloid of large molecular weight, together with starch granules, provides a synergistic effect that increases the molecular internal friction within a fluid matrix. The carboxylic groups of the pectin may also interact with calcium ions present in the nutritional composition, thus leading to an increase in viscosity, as the carboxylic groups of the pectin form a weak gel structure with the calcium ion(s), and also with peptides present in the nutritional composition. In some embodiments, the nutritional composition comprises a ratio of starch to pectin that is between about 12:1 and 20:1, respectively. In other embodiments, the ratio of starch to pectin is about 17:1. In some embodiments, the nutritional composition may comprise between about 0.05 and about 2.0% w/w pectin. In a particular embodiment, the nutritional composition may comprise about 0.5% w/w pectin.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

The nutritional composition may contain at least one acidic polysaccharide. An acidic polysaccharide, such as negatively charged pectin, may induce an anti-adhesive effect on pathogens in a subject's gastrointestinal tract. Indeed, nonhuman milk acidic oligosaccharides derived from pectin are able to interact with the epithelial surface and are known to inhibit the adhesion of pathogens on the epithelial surface.

In some embodiments, the nutritional composition comprises at least one pectin-derived acidic oligosaccharide. Pectin-derived acidic oligosaccharide(s) (pAOS) result from enzymatic pectinolysis, and the size of a pAOS depends on the enzyme use and on the duration of the reaction. In such embodiments, the pAOS may beneficially affect a subject's stool viscosity, stool frequency, stool pH and/or feeding tolerance. The nutritional composition of the present disclosure may comprise between about 2 g pAOS per liter of formula and about 6 g pAOS per liter of formula. In an embodiment, the nutritional composition comprises about 0.2 g pAOS/dL, corresponding to the concentration of acidic oligosaccharides in human milk. (Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, August 2005)

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiments, the nutritional composition comprises at least one additional carbohydrate source, that is, a carbohydrate component provided in addition to the aforementioned starch component. Additional carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can vary from between about 5 g and about 25 g/100 kcal. In some embodiments, the amount of carbohydrate is between about 6 g and about 22 g/100 kcal. In other embodiments, the amount of carbohydrate is between about 12 g and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

In one particular embodiment, the additional carbohydrate component of the nutritional composition is comprised of 100% lactose. In another embodiment, the additional carbohydrate component comprises between about 0% and 60% lactose. In another embodiment, the additional carbohydrate component comprises between about 15% and 55% lactose. In yet another embodiment, the additional carbohydrate component comprises between about 20% and 30% lactose. In these embodiments, the remaining source of carbohydrates may be any carbohydrate known in the art. In an embodiment, the carbohydrate component comprises about 25% lactose and about 75% corn syrup solids.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1 \times 10^4$ to about $1 \times 10^{10}$ colony forming units (cfu) per kg body weight per day. In another embodiment, the amount of the probiotic may vary from about $10^6$ to about $10^{10}$ cfu per kg body weight per day. In still another embodiment, the amount of the probiotic may vary from about $10^7$ to about $10^9$ cfu per day. In yet another embodiment, the amount of the probiotic may be at least about $10^6$ cfu per day. In certain embodiments, the nutritional composition comprises between about $1 \times 10^4$ to about $1.5 \times 10^{10}$ cfu of *Lactobacillus rhamnosus* GG per 100 kcal, more preferably from about $1 \times 10^6$ to about $1 \times 10^9$ cfu of *Lactobacillus rhamnosus* GG per 100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such new source is now known or later developed.

The nutritional composition of the disclosure may contain a source of long chain polyunsaturated fatty acid (LCPUFA) that comprises docosahexaenoic acid. Other suitable LCPUFAs include, but are not limited to, α-linoleic acid, γ-linoleic acid, linoleic acid, linolenic acid, eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The amount of long chain polyunsaturated fatty acid in the nutritional composition is advantageously at least about 5 mg/100 kcal, and may vary from about 5 mg/100 kcal to about 100 mg/100 kcal, more preferably from about 10 mg/100 kcal to about 50 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. Accordingly, the enhanced level of DHA of the nutritional composition may compensate for an existing nutritional DHA deficit.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally β-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6β-D-glucopyranosyl-1,3β-D-glucopyranose) or any mixture thereof.

In some embodiments, the amount of β-glucan present in the composition is at between about 0.010 and about 0.080 g per 100 g of composition. In other embodiments, the nutritional composition comprises between about 10 and about 30 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg β-glucan per day. The nutritional composition may be delivered in multiple doses to reach a target amount of β-glucan delivered to the subject throughout the day.

In some embodiments, the amount of β-glucan in the nutritional composition is between about 3 mg and about 17 mg per 100 kcal. In another embodiment the amount of β-glucan is between about 6 mg and about 17 mg per 100 kcal.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 kcal. The amount of protein typically can vary from about 1 to about 7 g/100 kcal. The amount of carbohydrate typically can vary from about 6 to about 22 g/100 kcal.

The nutritional composition of the present disclosure may further include at least one additional phytonutrient, that is, another phytonutrient component in addition to the pectin and/or starch components described hereinabove. Phytonutrients, or their derivatives, conjugated forms or precursors, that are identified in human milk are preferred for inclusion in the nutritional composition. Typically, dietary sources of carotenoids and polyphenols are absorbed by a nursing mother and retained in milk, making them available to nursing infants. Addition of these phytonutrients to infant or children's formulas allows such formulas to mirror the composition and functionality of human milk and to promote general health and well being.

For example, in some embodiments, the nutritional composition of the present disclosure may comprise, in an 8 fl. oz. (236.6 mL) serving, between about 80 and about 300 mg anthocyanins, between about 100 and about 600 mg proanthocyanidins, between about 50 and about 500 mg flavan-3-ols, or any combination or mixture thereof. In other embodiments, the nutritional composition comprises apple extract, grape seed extract, or a combination or mixture thereof. Further, the at least one phytonutrient of the nutritional composition may be derived from any single or blend of fruit, grape seed and/or apple or tea extract(s).

For the purposes of this disclosure, additional phytonutrients may be added to a nutritional composition in native, purified, encapsulated and/or chemically or enzymatically-modified form so as to deliver the desired sensory and stability properties. In the case of encapsulation, it is desirable that the encapsulated phytonutrients resist dissolution with water but are released upon reaching the small intestine. This could be achieved by the application of enteric coatings, such as cross-linked alginate and others.

Examples of additional phytonutrients suitable for the nutritional composition include, but are not limited to, anthocyanins, proanthocyanidins, flavan-3-ols (i.e. catechins, epicatechins, etc.), flavanones, flavonoids, isoflavonoids, stilbenoids (i.e. resveratrol, etc.) proanthocyanidins, anthocyanins, resveratrol, quercetin, curcumin, and/or any mixture thereof, as well as any possible combination of phytonutrients in a purified or natural form. Certain components, especially plant-based components of the nutritional compositions may provide a source of phytonutrients.

Some amounts of phytonutrients may be inherently present in known ingredients, such as natural oils, that are commonly used to make nutritional compositions for pediatric subjects. These inherent phytonutrient(s) may be but are not necessarily considered part of the phytonutrient component described in the present disclosure. In some embodiments, the phytonutrient concentrations and ratios as described herein are calculated based upon added and inherent phytonutrient sources. In other embodiments, the phytonutrient concentrations and ratios as described herein are calculated based only upon added phytonutrient sources.

In some embodiments, the nutritional composition comprises anthocyanins, such as, for example, glucosides of aurantinidin, cyanidin, delphinidin, europinidin, luteolinidin, pelargonidin, malvidin, peonidin, petunidin, and rosinidin. These and other anthocyanins suitable for use in the nutritional composition are found in a variety of plant sources. Anthocyanins may be derived from a single plant source or a combination of plant sources. Non-limiting examples of plants rich in anthocyanins suitable for use in the inventive composition include: berries (acai, grape, bilberry, blueberry, lingonberry, black currant, chokeberry, blackberry, raspberry, cherry, red currant, cranberry, crowberry, cloudberry, whortleberry, rowanberry), purple corn, purple potato, purple carrot, red sweet potato, red cabbage, eggplant.

In some embodiments, the nutritional composition of the present disclosure comprises proanthocyanidins, which include but are not limited to flavan-3-ols and polymers of flavan-3-ols (e.g., catechins, epicatechins) with degrees of polymerization in the range of 2 to 11. Such compounds may be derived from a single plant source or a combination of plant sources. Non-limiting examples of plant sources rich in proanthocyanidins suitable for use in the inventive nutritional composition include: grape, grape skin, grape seed, green tea, black tea, apple, pine bark, cinnamon, cocoa, bilberry, cranberry, black currant chokeberry.

Non-limiting examples of flavan-3-ols which are suitable for use in the inventive nutritional composition include catechin, epicatechin, gallocatechin, epigallocatechin, epicatechin gallate, epicatechin-3-gallate, epigallocatechin and gallate. Plants rich in the suitable flavan-3-ols include, but are not limited to, teas, red grapes, cocoa, green tea, apricot and apple.

Certain polyphenol compounds, in particular flavan-3-ols, may improve learning and memory in a human subject by increasing brain blood flow, which is associated with an increase and sustained brain energy/nutrient delivery as well as formation of new neurons. Polyphenols may also provide neuroprotective actions and may increase both brain synaptogenesis and antioxidant capability, thereby supporting optimal brain development in younger children.

Preferred sources of flavan-3-ols for the nutritional composition include at least one apple extract, at least one grape seed extract or a mixture thereof. For apple extracts, flavan-3-ols are broken down into monomers occurring in the range 4% to 20% and polymers in the range 80% to 96%. For grape seed extracts flavan-3-ols are broken down into monomers (about 46%) and polymers (about 54%) of the total favan-3-ols and total polyphenolic content. Preferred degree of polymerization of polymeric flavan-3-ols is in the range of between about 2 and 11. Furthermore, apple and grape seed extracts may contain catechin, epicatechin, epigallocatechin, epicatechin gallate, epigallocatechin gallate, polymeric proanthocyanidins, stilbenoids (i.e. resveratrol), flavonols (i.e. quercetin, myricetin), or any mixture thereof. Plant sources rich in flavan-3-ols include, but are not limited to apple, grape seed, grape, grape skin, tea (green or black), pine bark, cinnamon, cocoa, bilberry, cranberry, black currant, chokeberry.

If the nutritional composition is administered to a pediatric subject, an amount of flavan-3-ols, including monomeric flavan-3-ols, polymeric flavan-3-ols or a combination thereof, ranging from between about 0.01 mg and about 450 mg per day may be administered. In some cases, the amount of flavan-3-ols administered to an infant or child may range from about 0.01 mg to about 170 mg per day, from about 50 to about 450 mg per day, or from about 100 mg to about 300 mg per day.

In an embodiment of the disclosure, flavan-3-ols are present in the nutritional composition in an amount ranging from about 0.4 to about 3.8 mg/g nutritional composition (about 9 to about 90 mg/100 kcal). In another embodiment, flavan-3-ols are present in an amount ranging from about 0.8 to about 2.5 mg/g nutritional composition (about 20 to about 60 mg/100 kcal).

In some embodiments, the nutritional composition of the present disclosure comprises flavanones. Non-limiting examples of suitable flavanones include butin, eriodictyol, hesperetin, hesperidin, homeriodictyol, isosakuranetin, naringenin, naringin, pinocembrin, poncirin, sakuranetin, sakuranin, steurbin. Plant sources rich in flavanones include, but are not limited to orange, tangerine, grapefruit, lemon, lime. The nutritional composition may be formulated to deliver between about 0.01 and about 150 mg flavanones per day.

Moreover, the nutritional composition may also comprise flavonols. Flavonols from plant or algae extracts may be used. Flavonols, such as ishrhametin, kaempferol, myricetin, quercetin, may be included in the nutritional composition in amounts sufficient to deliver between about 0.01 and 150 mg per day to a subject.

The phytonutrient component of the nutritional composition may also comprise phytonutrients that have been identified in human milk, including but not limited to naringenin, hesperetin, anthocyanins, quercetin, kaempferol, epicatechin, epigallocatechin, epicatechin-gallate, epigallocatechin-gallate or any combination thereof. In certain embodiments, the nutritional composition comprises between about 50 and about 2000 nmol/L epicatechin, between about 40 and about 2000 nmol/L epicatechin gallate, between about 100 and about 4000 nmol/L epigallocatechin gallate, between about 50 and about 2000 nmol/L naringenin, between about 5 and about 500 nmol/L kaempferol, between about 40 and about 4000 nmol/L hesperetin, between about 25 and about 2000 nmol/L anthocyanins, between about 25 and about 500 nmol/L quercetin, or a mixture thereof. Furthermore, the nutritional composition may comprise the metabolite(s) of a phytonutrient or of its parent compound, or it may comprise other classes of dietary phytonutrients, such as glucosinolate or sulforaphane.

In certain embodiments, the nutritional composition comprises carotenoids, such as lutein, zeaxanthin, astaxanthin, lycopene, beta-carotene, alpha-carotene, gamma-carotene, and/or beta-cryptoxanthin. Plant sources rich in carotenoids include, but are not limited to kiwi, grapes, citrus, tomatoes, watermelons, papayas and other red fruits, or dark greens, such as kale, spinach, turnip greens, collard greens, romaine lettuce, broccoli, zucchini, garden peas and Brussels sprouts, spinach, carrots.

Humans cannot synthesize carotenoids, but over 34 carotenoids have been identified in human breast milk, including isomers and metabolites of certain carotenoids. In addition to their presence in breast milk, dietary carotenoids, such as alpha and beta-carotene, lycopene, lutein, zeaxanthin, astaxanthin, and cryptoxanthin are present in serum of lactating women and breastfed infants. Carotenoids in general have been reported to improve cell-to-cell communication, promote immune function, support healthy respiratory health, protect skin from UV light damage, and have been linked to reduced risk of certain types of cancer, and all-cause mortality. Furthermore, dietary sources of carotenoids and/or polyphenols are absorbed by human subjects, accumulated and retained in breast milk, making them available to nursing infants. Thus, addition of phytonutrients to infant formulas or children's products would bring the formulas closer in composition and functionality to human milk.

Flavonoids, as a whole, may also be included in the nutritional composition, as flavonoids cannot be synthesized by humans. Moreover, flavonoids from plant or algae extracts may be useful in the monomer, dimer and/or polymer forms. In some embodiments, the nutritional composition comprises levels of the monomeric forms of flavonoids similar to those in human milk during the first three months of lactation. Although flavonoid aglycones (monomers) have been identified in human milk samples, the conjugated forms of flavonoids and/or their metabolites may also be useful in the nutritional composition. The flavonoids could be added in the following forms: free, glucuronides, methyl glucuronides, sulphates, and methyl sulphates.

The nutritional composition may also comprise isoflavonoids and/or isoflavones. Examples include, but are not limited to, genistein (genistin), daidzein (daidzin), glycitein, biochanin A, formononetin, coumestrol, irilone, orobol, pseudobaptigenin, anagyroidisoflavone A and B, calycosin, glycitein, irigenin, 5-O-methylgenistein, pratensein, prunetin, psi-tectorigenin, retusin, tectorigenin, iridin, ononin, puerarin, tectoridin, derrubone, luteone, wighteone, alpinumisoflavone, barbigerone, di-O-methylalpinumisoflavone, and 4'-methyl-alpinumisoflavone. Plant sources rich in isoflavonoids, include, but are not limited to, soybeans, psoralea, kudzu, lupine, fava, chick pea, alfalfa, legumes and peanuts. The nutritional composition may be formulated to deliver between about 0.01 and about 150 mg isoflavones and/or isoflavonoids per day.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure further provides a method for providing nutritional support to a subject. The method includes administering to the subject an effective amount of the nutritional composition of the present disclosure.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. Each nutritional composition comprises a hydrolyzed protein, at least one pre-gelatinized starch, and at least one pectin. In certain embodiments, the nutritional compositions of the feeding regimen may also include a source of long chain polyunsaturated fatty acid, at least one prebiotic, an iron source, a source of β-glucan, vitamins or minerals, lutein, zeaxanthin, or any other ingredient described hereinabove. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

EXAMPLE 1

This example illustrates an embodiment of a nutritional product according to the present disclosure.

| Description | kg per 100 kg |
|---|---|
| carbohydrate, total | 38.9 |
| protein, total | 28.8 |
| fat, total | 25.6 |
| prebiotics | 4.5 |
| soy lecithin | 0.8 |
| lactoferrin | 0.3 |
| calcium carbonate | 0.5 |
| potassium citrate | 0.2 |
| ferrous sulfate | 0.05 |
| potassium chloride | 0.048 |
| magnesium oxide | 0.023 |
| sodium chloride | 0.025 |
| zinc sulfate | 0.015 |
| cupric sulfate | 0.002 |
| manganese sulfate | 0.0003 |
| sodium selenite | 0.00003 |
| choline chloride | 0.144 |
| ascorbic acid | 0.093 |
| Niacinamide | 0.006 |

| Description | kg per 100 kg |
|---|---|
| calcium pantothenate | 0.003 |
| vitamin A palmitate | 0.007 |
| vitamin B12 | 0.002 |
| vitamin D3 | 0.000001 |
| Riboflavin | 0.0008 |
| thiamin | 0.0006 |
| vitamin B6 | 0.0004 |
| folic acid | 0.0001 |
| vitamin K1 | 0.006 |
| biotin | 0.00002 |
| inositol | 0.03 |
| vitamin E acetate | 0.01 |
| taurine | 0.05 |
| L-carnitine | 0.001 |

EXAMPLE 2

This example illustrates another embodiment of a nutritional product according to the present disclosure.

| Description | kg per 100 kg |
|---|---|
| carbohydrate, total | 24.7 |
| protein, total | 31.9 |
| fat, total | 39.3 |
| prebiotics | 3.6 |
| lactoferrin | 0.1 |
| calcium carbonate | 0.15 |
| ferrous sulfate | 0.03 |
| zinc sulfate | 0.01 |
| copper sulfate | 0.00025 |
| manganese sulfate | 0.0002 |
| sodium selenite | 0.00001 |
| choline bitartrate | 0.05 |
| ascorbic acid | 0.004 |
| sodium ascorbate | 0.04 |
| niacinamide | 0.007 |
| calcium pantothenate | 0.0005 |
| vitamin A palmitate | 0.0005 |
| vitamin D3 | 0.0002 |
| riboflavin | 0.0001 |
| thiamin | 0.00005 |
| vitamin B6 | 0.00005 |
| folic acid | 0.000067 |
| vitamin K1 | 0.00002 |
| vitamin E acetate | 0.008 |
| taurine | 0.02 |
| fish oil | 0.2 |
| B-glucan | 0.03 |

EXAMPLE 3

This example illustrates one embodiment of ingredients that can be used to prepare the nutritional product according to the present disclosure.

| water | 872 ml |
|---|---|
| lactose | 65.6 mg |
| vegetable oil blend | 353.0 mg |
| nonfat milk evaporated | 34.0 mg |
| whey protein concentrate | 8.5 mg |
| galacto-oligosaccharide | 4.7 mg |
| casein | 3.5 mg |
| polydextrose | 2.4 mg |
| lactoferrin solution (10%) | 1.0 mg |
| single cell DHA and ARA oil blend | 0.94 mg |
| mono- and di-glycerides | 0.7 mg |
| calcium carbonate | 0.44 mg |
| calcium phosphate | 0.4 mg |
| potassium citrate | 0.4 mg |
| potassium chloride | 0.4 mg |
| soy lecithin | 0.4 mg |
| sodium chloride | 0.3 mg |
| potassium phosphate | 0.3 mg |
| choline chloride | 0.2 mg |
| magnesium oxide | 0.08 mg |
| calcium hydroxide | 0.08 mg |
| ferrous sulfate | 0.07 mg |

EXAMPLE 4

This example illustrates another embodiment of ingredients that can be used to prepare the nutritional product according to the present disclosure.

| water | 686 ml |
|---|---|
| reduced minerals whey | 215 mg |
| nonfat milk evaporated | 67 mg |
| vegetable oil blend | 33 mg |
| lactose | 17 mg |
| galacto-oligosaccharide | 4.7 mg |
| polydextrose | 2.4 mg |
| lactoferrin solution (10%) | 1.0 mg |
| single cell DHA and ARA oil blend | 0.9 mg |
| mono- and di-glycerides | 0.7 mg |
| calcium carbonate | 0.44 mg |
| calcium phosphate | 0.4 mg |
| potassium citrate | 0.4 mg |
| potassium chloride | 0.4 mg |
| soy lecithin | 0.4 mg |
| potassium phosphate | 0.3 mg |
| carrageenan | 0.3 mg |
| sodium citrate | 0.2 mg |
| choline chloride | 0.2 mg |
| magnesium oxide | 0.08 mg |
| calcium chloride | 0.08 mg |
| ferrous sulfate | 0.07 mg |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A method for reducing the occurrence of anxiety and depression-related behaviors in a pediatric subject, the method comprising administering to the pediatric subject a nutritionally complete milk-based nutritional composition comprising:
   (a) lactoferrin from a non-human source present at a level of about 70 mg/100 kcal to about 220 mg/100 kcal;
   (b) a prebiotic component about 0.1 g/100 kcal to about 1 g/100 kcal, wherein the prebiotic component comprises polydextrose and a galactooligosaccharide, where the polydextrose comprises at least 20% of the prebiotic component; and
   (c) at least one probiotic comprising *Lactobacillus rhamnosus* GG, the probiotic present at a level of from $1\times10^4$ to $1\times10^{10}$ cfu per kg body weight per day.

2. The method according to claim 1, wherein the lactoferrin is bovine lactoferrin.

3. The method according to claim 1, wherein the nutritional composition is an infant formula.

4. The method according to claim 1, wherein the nutritional composition additionally comprises about 3 g/100 kcal to about 7 g/100 kcal of a fat source.

5. The method according to claim 1, wherein the nutritional composition additionally comprises about 1 g/100 kcal to about 5 g/100 kcal of a protein source.

6. The method of claim 1, wherein the nutritional composition further comprises a source of long chain polyunsaturated fatty acids.

7. The method of claim 6, wherein the source of long chain polyunsaturated fatty acids comprises docosahexaenoic acid.

8. The method of claim 7, wherein the source of long chain polyunsaturated fatty acids further comprises arachidonic acid.

9. The method of claim 8, the weight ratio of docosahexaenoic acid to arachidonic acid is from about 1:3 to about 9:1.

10. The method of claim 6, wherein the amount of long chain polyunsaturated fatty acid in the nutritional composition is from about 5 mg/100 kcal to about 100 mg/100 kcal.

* * * * *